United States Patent
Scirica

(10) Patent No.: US 11,141,157 B2
(45) Date of Patent: *Oct. 12, 2021

(54) GRASPING JAW MECHANISM

(71) Applicant: Covidien LP, Mansfield, MA (US)

(72) Inventor: Paul Scirica, Huntington, CT (US)

(73) Assignee: Covidien LP, Mansfield, MA (US)

(*) Notice: Subject to any disclaimer, the term of this patent is extended or adjusted under 35 U.S.C. 154(b) by 140 days.

This patent is subject to a terminal disclaimer.

(21) Appl. No.: 16/576,024

(22) Filed: Sep. 19, 2019

(65) Prior Publication Data

US 2020/0008805 A1 Jan. 9, 2020

Related U.S. Application Data

(63) Continuation of application No. 15/166,481, filed on May 27, 2016, now Pat. No. 10,441,282, which is a (Continued)

(51) Int. Cl.
*A61B 17/072* (2006.01)
*A61B 17/068* (2006.01)
(Continued)

(52) U.S. Cl.
CPC .. *A61B 17/07207* (2013.01); *A61B 17/00234* (2013.01); *A61B 17/068* (2013.01);
(Continued)

(58) Field of Classification Search
CPC .......... A61B 17/0686; A61B 17/07207; A61B 17/00234; A61B 17/068;
(Continued)

(56) References Cited

U.S. PATENT DOCUMENTS

| 4,471,781 A | 9/1984 | Di Giovanni et al. |
| 5,290,299 A | 3/1994 | Fain et al. |

(Continued)

FOREIGN PATENT DOCUMENTS

| WO | 2004112618 A2 | 12/2004 |
| WO | 2005037329 A2 | 4/2005 |

OTHER PUBLICATIONS

International Search Report from corresponding EP Appl. No. 12154546.1 dated Oct. 29, 2012.

(Continued)

*Primary Examiner* — Thomas M Wittenschlaeger
(74) *Attorney, Agent, or Firm* — Carter, DeLuca & Farrell, LLP

(57) ABSTRACT

A surgical device is disclosed which includes a handle assembly, an elongated member and a disposable loading unit. The handle assembly includes a mode selection mechanism configured to alternate the surgical device between a first grasping mode of operation and a second clamping mode of operation. The handle assembly includes a rotation control member and an articulation lever. The rotation control member is configured to facilitate rotation of the elongated member with respect to the handle assembly. The articulation lever is configured to facilitate articulation of the tool assembly about an axis substantially perpendicular to the longitudinal axis of elongated member. In one embodiment, the tool assembly includes a cartridge assembly having a plurality of staples and an anvil assembly configured to clamp and staple tissue in the second clamping mode of operation of the device.

14 Claims, 12 Drawing Sheets

Related U.S. Application Data continuation of application No. 13/688,525, filed on Nov. 29, 2012, now Pat. No. 9,364,218, which is a continuation of application No. 11/544,061, filed on Oct. 6, 2006, now Pat. No. 8,336,751.

(51) Int. Cl.
*A61B 17/00* (2006.01)
*A61B 17/29* (2006.01)

(52) U.S. Cl.
CPC *A61B 17/0686* (2013.01); *A61B 2017/00367* (2013.01); *A61B 2017/2919* (2013.01); *A61B 2017/2927* (2013.01); *A61B 2017/2929* (2013.01)

(58) Field of Classification Search
CPC .. A61B 2017/00367; A61B 2017/2929; A61B 2017/2919; A61B 2017/2927
See application file for complete search history.

(56) References Cited

U.S. PATENT DOCUMENTS

| | | | |
|---|---|---|---|
| 5,307,976 A | | 5/1994 | Olson et al. |
| 5,336,229 A | | 8/1994 | Noda |
| 5,344,061 A | | 9/1994 | Crainich |
| 5,383,881 A | | 1/1995 | Green et al. |
| 5,403,312 A | | 4/1995 | Yates et al. |
| 5,405,073 A | | 4/1995 | Porter |
| 5,431,669 A | | 7/1995 | Thompson et al. |
| 5,449,365 A | * | 9/1995 | Green ................ A61B 17/1285 606/142 |
| 5,452,836 A | | 9/1995 | Huitema et al. |
| 5,465,894 A | | 11/1995 | Clark et al. |
| 5,465,895 A | | 11/1995 | Knodel et al. |
| 5,487,500 A | | 1/1996 | Knodel et al. |
| 5,529,235 A | | 6/1996 | Boiarski et al. |
| 5,547,117 A | | 8/1996 | Hamblin et al. |
| 5,553,765 A | | 9/1996 | Knodel et al. |
| 5,597,107 A | | 1/1997 | Knodel et al. |
| 5,605,272 A | | 2/1997 | Witt et al. |
| 5,632,432 A | | 5/1997 | Schulze et al. |
| 5,643,289 A | | 7/1997 | Sauer et al. |
| 5,697,543 A | | 12/1997 | Burdorff |
| 5,706,997 A | * | 1/1998 | Green ................ A61B 17/072 227/175.2 |
| 5,713,505 A | | 2/1998 | Huitema |
| 5,762,255 A | | 6/1998 | Chrisman et al. |
| 5,814,055 A | | 9/1998 | Knodel et al. |
| 5,823,066 A | | 10/1998 | Huitema et al. |
| 5,846,254 A | | 12/1998 | Schulze et al. |
| 5,855,311 A | | 1/1999 | Hamblin et al. |
| 5,865,361 A | * | 2/1999 | Milliman ............ A61B 17/072 227/176.1 |
| 6,032,849 A | * | 3/2000 | Mastri .............. A61B 17/07207 227/176.1 |
| 6,109,500 A | * | 8/2000 | Alli ................ A61B 17/07207 227/175.2 |
| H1904 H | | 10/2000 | Yates et al. |
| 6,592,597 B2 | | 7/2003 | Grant et al. |
| 6,656,193 B2 | | 12/2003 | Grant et al. |
| 6,743,240 B2 | | 6/2004 | Smith et al. |
| 6,755,338 B2 | | 6/2004 | Hahnen et al. |
| 6,786,382 B1 | | 9/2004 | Hoffman |
| 6,805,273 B2 | | 10/2004 | Bilotti et al. |
| 6,824,548 B2 | | 11/2004 | Smith et al. |
| 6,843,794 B2 | | 1/2005 | Sixto, Jr. et al. |
| 6,905,057 B2 | | 6/2005 | Swayze et al. |
| 6,945,979 B2 | | 9/2005 | Kortenbach et al. |
| 6,959,852 B2 | | 11/2005 | Shelton, IV et al. |
| 6,964,363 B2 | | 11/2005 | Wales et al. |
| 6,978,921 B2 | | 12/2005 | Shelton, IV et al. |
| 6,981,628 B2 | | 1/2006 | Wales |
| 6,988,649 B2 | | 1/2006 | Shelton, IV et al. |
| 6,988,650 B2 | | 1/2006 | Schwemberger et al. |
| 7,000,818 B2 | | 2/2006 | Shelton, IV et al. |
| 7,000,819 B2 | | 2/2006 | Swayze et al. |
| 7,121,446 B2 | | 10/2006 | Arad et al. |
| 7,159,750 B2 | | 1/2007 | Racenet et al. |
| 7,328,829 B2 | | 2/2008 | Arad et al. |
| 7,487,899 B2 | * | 2/2009 | Shelton, IV ..... A61B 17/07207 227/175.1 |
| 7,963,431 B2 | | 6/2011 | Scirica |
| 10,441,282 B2 | | 10/2019 | Scirica |
| 2002/0068947 A1 | * | 6/2002 | Kuhns ................ A61B 17/0644 606/143 |
| 2002/0099388 A1 | | 7/2002 | Mayenberger |
| 2002/0198537 A1 | | 12/2002 | Smith et al. |
| 2003/0009193 A1 | | 1/2003 | Corsaro |
| 2003/0191478 A1 | | 10/2003 | Kortenbach et al. |
| 2004/0193185 A1 | | 9/2004 | McBrayer |
| 2004/0193186 A1 | | 9/2004 | Kortenbach et al. |
| 2004/0199180 A1 | | 10/2004 | Knodel et al. |
| 2004/0199181 A1 | | 10/2004 | Knodel et al. |
| 2004/0232195 A1 | | 11/2004 | Shelton et al. |
| 2004/0232199 A1 | | 11/2004 | Shelton et al. |
| 2004/0232201 A1 | * | 11/2004 | Wenchell ............ A61B 17/068 227/176.1 |
| 2005/0006431 A1 | | 1/2005 | Shelton et al. |
| 2005/0006432 A1 | * | 1/2005 | Racenet ............ A61B 17/068 227/176.1 |
| 2005/0006434 A1 | | 1/2005 | Wales et al. |
| 2005/0070925 A1 | | 3/2005 | Shelton et al. |
| 2005/0072827 A1 | | 4/2005 | Mollenauer |
| 2005/0103819 A1 | * | 5/2005 | Racenet ............ A61B 17/068 227/175.1 |
| 2005/0139632 A1 | | 6/2005 | Schwemberger et al. |
| 2005/0139633 A1 | | 6/2005 | Wukusick et al. |
| 2005/0139634 A1 | | 6/2005 | Schwemberger et al. |
| 2005/0139635 A1 | | 6/2005 | Wukusick et al. |
| 2005/0139636 A1 | | 6/2005 | Schwemberger et al. |
| 2005/0143759 A1 | | 6/2005 | Kelly |
| 2005/0145672 A1 | | 7/2005 | Schwemberger et al. |
| 2005/0145673 A1 | | 7/2005 | Nguyen et al. |
| 2005/0165415 A1 | | 7/2005 | Wales |
| 2005/0173490 A1 | * | 8/2005 | Shelton, IV ..... A61B 17/07207 227/175.2 |
| 2005/0178813 A1 | | 8/2005 | Swayze et al. |
| 2005/0187576 A1 | | 8/2005 | Whitman et al. |
| 2005/0247752 A1 | | 11/2005 | Kelly et al. |
| 2005/0247753 A1 | | 11/2005 | Kelly et al. |
| 2005/0263562 A1 | | 12/2005 | Shelton et al. |
| 2006/0000867 A1 | | 1/2006 | Shelton et al. |
| 2006/0000868 A1 | | 1/2006 | Shelton et al. |
| 2006/0022014 A1 | | 2/2006 | Shelton et al. |
| 2006/0022015 A1 | | 2/2006 | Shelton et al. |
| 2006/0049230 A1 | | 3/2006 | Shelton et al. |
| 2006/0060630 A1 | * | 3/2006 | Shelton, IV ..... A61B 17/07207 227/175.2 |
| 2006/0124689 A1 | | 6/2006 | Arad et al. |
| 2007/0034670 A1 | | 2/2007 | Racenet et al. |
| 2007/0060952 A1 | | 3/2007 | Roby et al. |
| 2011/0240713 A1 | | 10/2011 | Scirica et al. |
| 2011/0272448 A1 | | 11/2011 | Scirica et al. |

OTHER PUBLICATIONS

European Search Report for EP 07253976.0-2310 date of completion is Jan. 28, 2008 (9 pages).
Australian Examination Report from Appl. No. 2014221280 dated Oct. 7, 2015.
Canadian Examination Report dated Apr. 5, 2017 in Appl. No. CA 2,895,725.
Canadian Office Action dated Jun. 4, 2019, issued in Canadian Appln. No. 3,003,793.

* cited by examiner

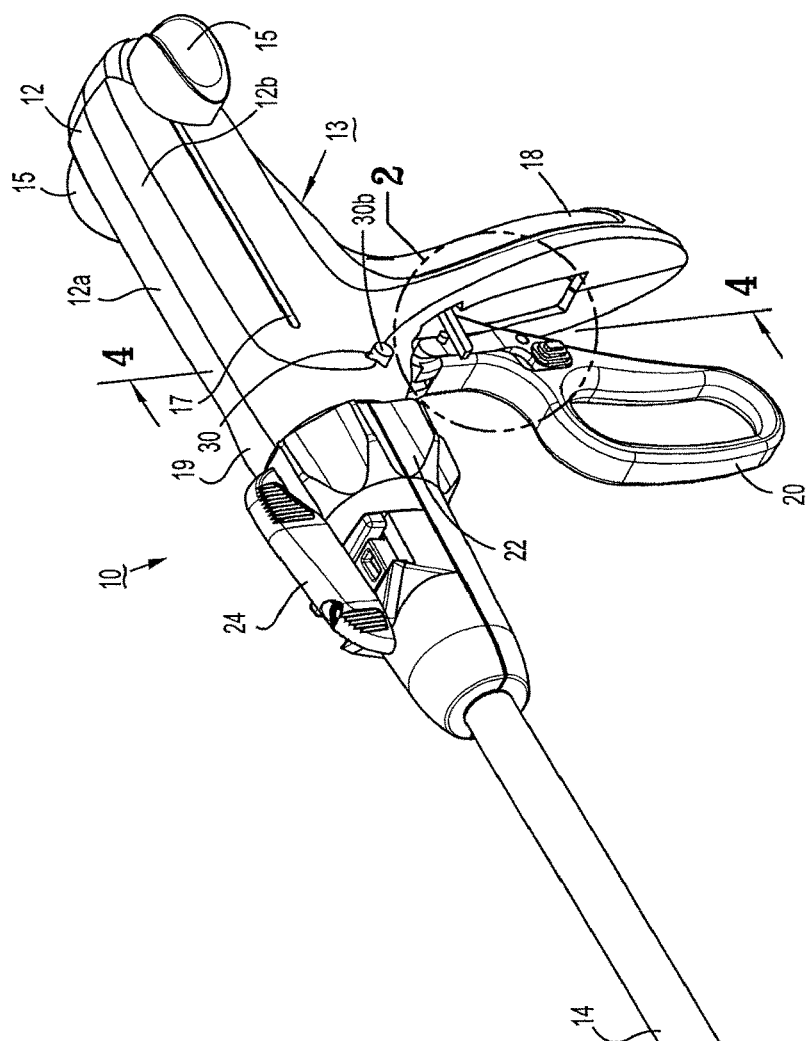
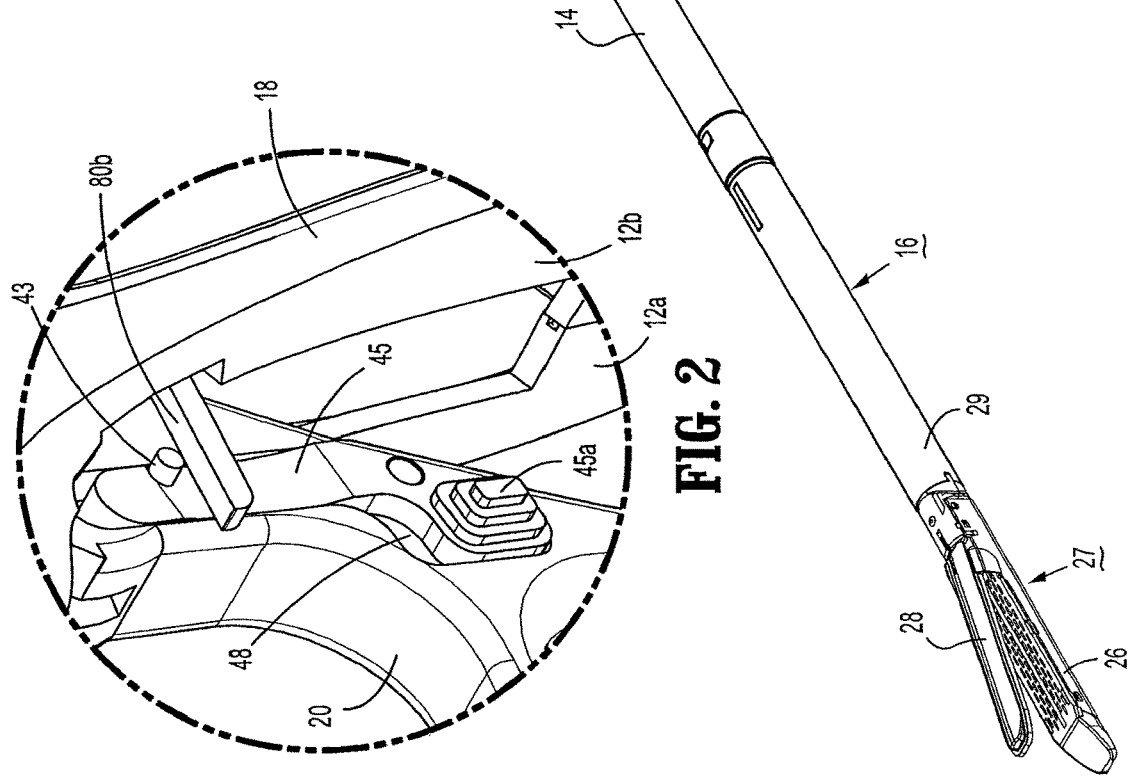
FIG. 1
FIG. 2

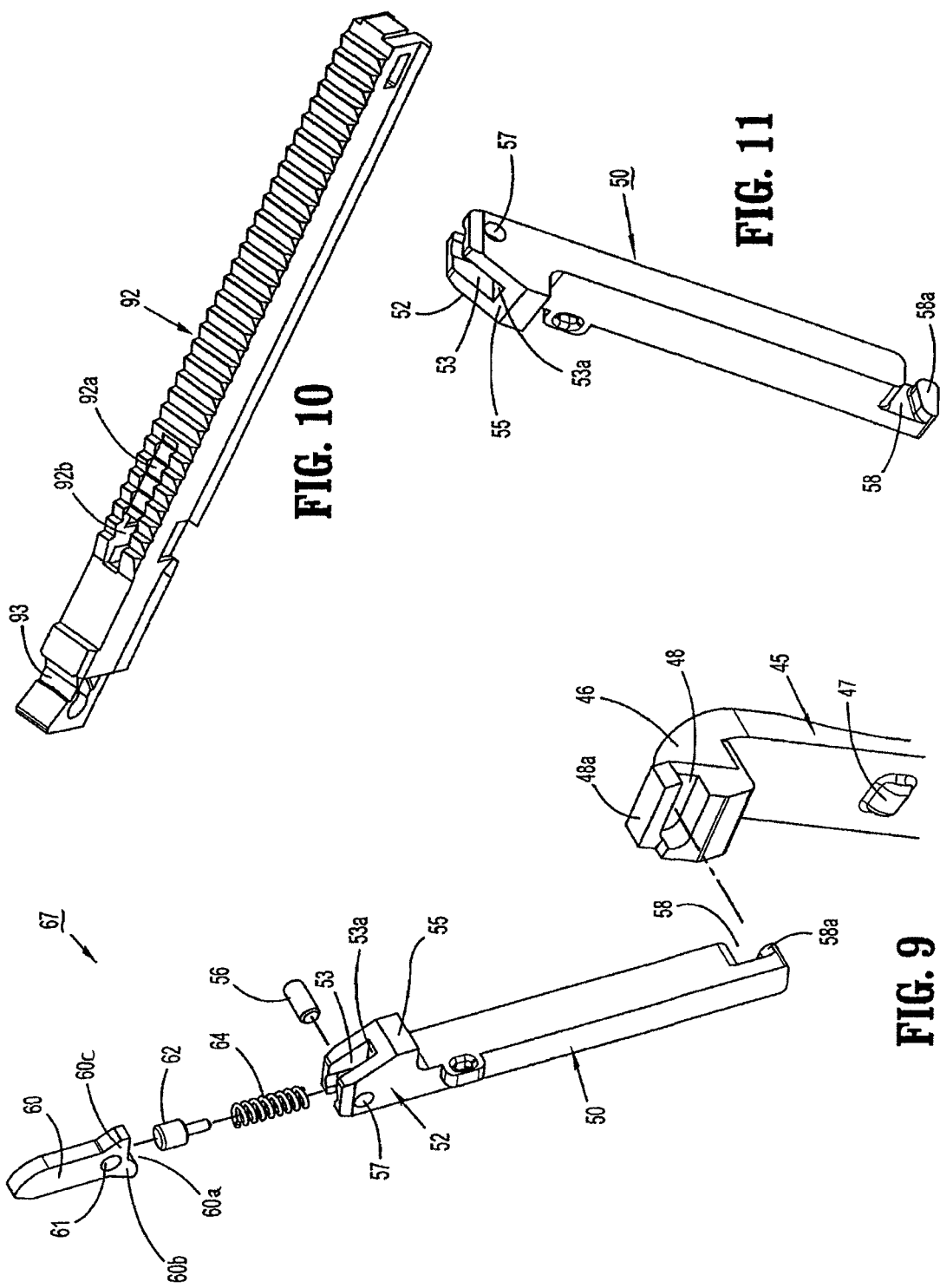

GRASPING JAW MECHANISM

CROSS-REFERENCE TO RELATED APPLICATIONS

This application is a continuation of U.S. patent application Ser. No. 15/166,481, filed May 27, 2016, which is a continuation of U.S. patent application Ser. No. 13/688,525, filed Nov. 29, 2012 which claims the benefit of and priority to U.S. patent application Ser. No. 11/544,061 filed Oct. 6, 2006, now U.S. Pat. No. 8,336,751, the entire disclosures each of which are incorporated by reference herein.

BACKGROUND

Technical Field

The present disclosure relates to a surgical stapling device and, more particularly, to an endoscopic surgical stapling device configured to operate a tool assembly in a grasping mode independent of a clamping and/or firing mode.

Background of Related Art

Surgical devices wherein tissue is first grasped or clamped between opposing jaw structure and then joined by surgical fasteners are well known in the art. The fasteners are typically in the form of surgical staples, but two-part polymeric fasteners can also be utilized.

Instruments for this purpose can include a tool assembly with two elongated members which are respectively used to capture or clamp tissue. Typically, one of the members carries a staple cartridge which houses a plurality of staples arranged, for example, in at least two lateral rows while the other member has an anvil that defines a surface for forming the staple legs as the staples are driven from the staple cartridge. In some staplers, the stapling operation is effected by cam bars that travel longitudinally through the staple cartridge, with the cam bars acting upon staple pushers for sequentially ejecting the staples from the staple cartridge. A knife can travel between the staple rows for longitudinally cutting the stapled tissue between the rows of staples. Such staplers are disclosed in U.S. Pat. Nos. 6,250,532 and 6,241,139, each of which are currently owned by Tyco Healthcare Group LP, and are incorporated herein by reference in their entirety.

In endoscopic or laparoscopic procedures, surgery is performed through small incisions or through small diameter cannulas inserted through small entrance wounds in the skin. Due to the limited degree of motion of an instrument when it is positioned through the skin, it may be quite difficult for a surgeon to manipulate the tool assembly of the instrument around body tissue to access and/or clamp the tissue site. Instruments having rotatable endoscopic body portions and rotatable and/or articulatable tool assemblies have been developed to overcome this problem and are commercially available. Although these instruments provide significant improvements in the endoscopic tool art, further improvements that may decrease the time required for surgical procedures and allow easier access to tissue sites are desired.

Accordingly, a continuing need exists for an endoscopic or laparoscopic surgical device having a tool assembly which can be quickly and easily manipulated between different modes of operation.

SUMMARY

In accordance with the present disclosure, a surgical stapling device is provided which includes a handle assembly having a movable handle, an elongated member, and a disposable loading unit ("DLU"). The DLU includes a tool assembly positioned at a distal end having an anvil assembly and a cartridge assembly. The elongated member is rotatably secured to the handle assembly. The tool assembly is a stapling device and the handle assembly includes a grasping pawl which is movable into engagement with an actuation shaft to allow the tool assembly to be operated in a grasper mode. More specifically, the grasping pawl is manipulated by a pair of slide buttons slidably positioned on opposed sides of the handle assembly and is selectively movable into engagement with the actuation shaft to allow the actuation shaft to move a distance which will, upon operation of the movable handle, effect approximation of cartridge and anvil assemblies of the tool assembly, but will not affect the firing of staples.

In another aspect of the disclosure, a rotation control member is rotatably mounted to the forward end of the handle assembly to facilitate rotation of elongated member with respect to the handle assembly.

In yet another aspect of the disclosure, an articulation lever is mounted adjacent the rotation control member to facilitate articulation of the tool assembly.

BRIEF DESCRIPTION OF THE DRAWINGS

Embodiments of the presently disclosed surgical stapling device are disclosed herein with reference to the drawings wherein:

FIG. 1 is a side perspective view of the presently disclosed surgical stapling device;

FIG. 2 is an enlarged view of the indicated area of detail shown in FIG. 1;

FIG. 9 is an enlarged view of the indicated area of detail shown in FIG. 3;

FIG. 10 is a bottom perspective view of the toothed rack of FIG. 3;

FIG. 11 is a side perspective view of the grasping pawl arm rotated 90. degree. from the depiction shown in FIG. 9;

DETAILED DESCRIPTION OF THE EMBODIMENTS

Figure 3:
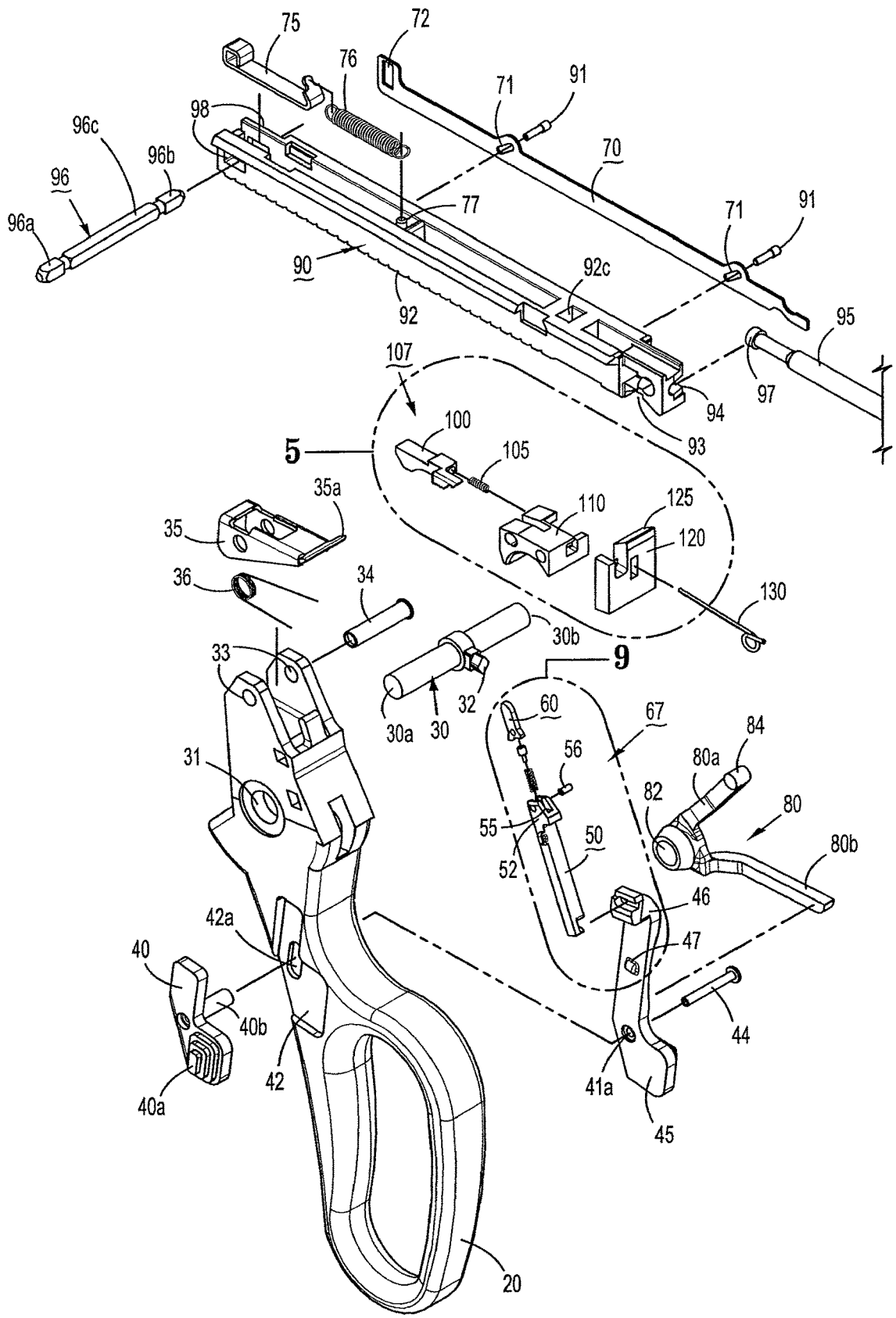
FIG. 3 is a side perspective view of the proximal end of the surgical stapling device shown in FIG. 1, with parts separated.

Embodiments of the presently disclosed grasping jaw mechanism will now be described in detail with reference to the drawings in which like reference numerals designate identical or corresponding element in each of the several views.

Throughout this description, the term "proximal" will refer to the portion of the device closest to the operator and the term "distal" will refer to the portion of the device furthest from the operator.

FIG. 1 illustrates one embodiment of the presently disclosed surgical stapling device shown generally as 10. Surgical stapling device 10 includes a handle assembly 13, an elongated member 14 extending distally from handle assembly 13, and a disposable loading unit ("DLU") 16 releasably secured to a distal end of elongated member 14. DLU 16 includes a proximal body portion 29 which forms an extension of elongated member 14, and a distal tool assembly 27 including a cartridge assembly 26 and an anvil assembly 28. Cartridge assembly 26 and anvil assembly 28 further define a pair of jaws. Tool assembly 27 is pivotally connected to body portion 29 about an axis substantially perpendicular to the longitudinal axis of elongated member 14. Cartridge assembly 26 houses a plurality of staples. Anvil assembly 28 is movable in relation to cartridge assembly 26 between an open position spaced from cartridge assembly 26 and an approximated or clamped position in juxtaposed alignment with cartridge assembly 26. Tool assembly 27 may alternatively be arranged such that cartridge assembly 26 is movable in relation to anvil assembly 28. DLU 16 is configured to apply linear rows of staples measuring from about 30 mm to about 60 mm in length. DLU's having linear rows of staples of other lengths are also envisioned, e.g., 45 mm.

Handle assembly 13 includes a stationary handle 18, a movable handle 20, and a barrel portion 19. A rotation control member 22 is rotatably mounted at the forward end of barrel portion 19 to facilitate rotation of elongated member 14 with respect to handle assembly 13. Rotation control member 22 is formed from molded plastic half-sections 12a and 12b, although other materials, e.g., metals, and manufacturing methods are envisioned. An articulation lever 24 is also mounted on the forward end of barrel portion 19 adjacent rotation control member 22 to facilitate articulation of tool assembly 30. U.S. Pat. No. 5,865,361 to Milliman et al., which is owned by Tyco Healthcare, LP, describes a rotation control assembly and articulation assembly for a surgical stapling apparatus and is hereby incorporated herein by reference in its entirety.

A pair of retractor knobs 15 is movably positioned along barrel portion 19 to return device 10 to a retracted position, as will be described in detail below (see FIG. 1). A pair of recesses 42 and 48 (see FIG. 2) in opposed lateral faces of movable handle 20 are dimensioned for slidably receiving slide buttons 40 and 45, respectively (see FIG. 3). Slide button 40 is operatively associated with slide button 45, such that movement of one effects movement of the other. Slide buttons 40 and 45 are configured to alternate device 10 between a "grasping" mode and a "firing" or clamping mode. In grasping mode, tool assembly 27 is configured to operate as a grasping jaw mechanism, i.e., anvil assembly 28 is movable in relation to cartridge assembly 26 to grasp tissue therebetween, back and forth between open and approximated positions. In clamping mode, tool assembly 27 is configured to operate as a clamping mechanism, i.e., anvil assembly 28 is movable in relation to cartridge assembly 26 to grasp tissue therebetween and apply linear rows of staples. In the clamping mode, the user can retract retractor knobs 15 to open tool assembly 27 and release the tissue. Slide buttons 40 and 45 each include a raised surface 40a and 45a, respectively. Raised surfaces 40a and 45a are configured to be engaged by the surgeon's finger to move slide buttons 40 and 45 within recesses 42 and 48, respectively. As to be appreciated, alternatives to slide buttons 40 and 45 are also contemplated, e.g., knobs, levers, depressible buttons, toggles, trigger assemblies, etc.

Handle assembly 13 includes a housing 12 formed from a pair of molded half-sections 12a and 12b, which forms stationary handle 18 and barrel portion 19 of handle assembly 13. Half-sections 12a and 12b are formed of a thermoplastic material, e.g., polycarbonate. Alternately, other materials having the requisite strength requirements may be used to form housing 12, e.g., surgical grade metals. Housing 12 half-sections 12a and 12b are secured to each other using known fastening techniques, e.g., adhesives, welding, interlocking structure, screws, etc. Alternately, other fastening techniques may be used.

Referring to FIG. 3, movable handle 20 is rotatably supported between housing half-sections 12a and 12b about a cylindrical member (not shown) which is received within an opening 31 within movable handle 20. A biasing member (not shown), e.g., a torsion spring, may be included to urge movable handle 20 away from stationary handle 18 to a non-compressed position. Movable handle 20 includes a pair of throughbores 33 dimensioned to receive a pivot member 34. An advancement pawl 35 is rotatably supported on pivot member 34 and is biased by a spring 36 towards an actuation shaft 90.

Actuation shaft 90 is slidably supported between retracted and advanced positions within barrel portion 19 of housing 12 and includes a distal end defining a recess 94 configured to rotatably receive the proximal end 97 of a control rod 95. Actuation shaft 90 includes a toothed rack 92. Advancement pawl 35 has an engagement finger 35a which is biased by spring 36 towards toothed rack 92 of actuation shaft 90. When movable handle 20 is actuated, i.e., is pivoted towards stationary handle 18 against the bias of a torsion spring (not shown), engagement finger 35a of pawl 35 engages toothed rack 92 of actuation shaft 90 to advance actuation shaft 90 and control rod 95 distally.

Figure 15:
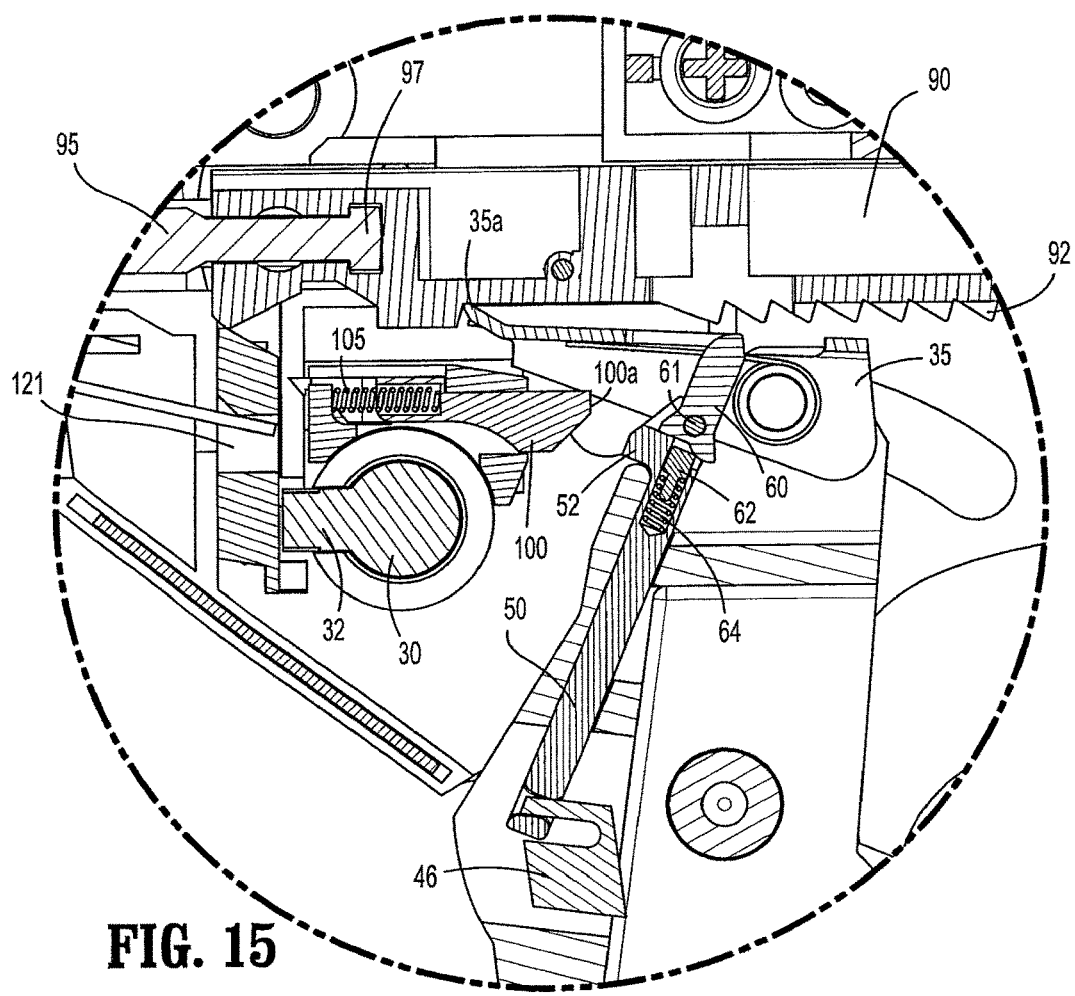
FIG. 15 is an enlarged view of the indicated area of detail shown in FIG. 14, illustrating the handle assembly in clamping/firing mode.
Figure 16:
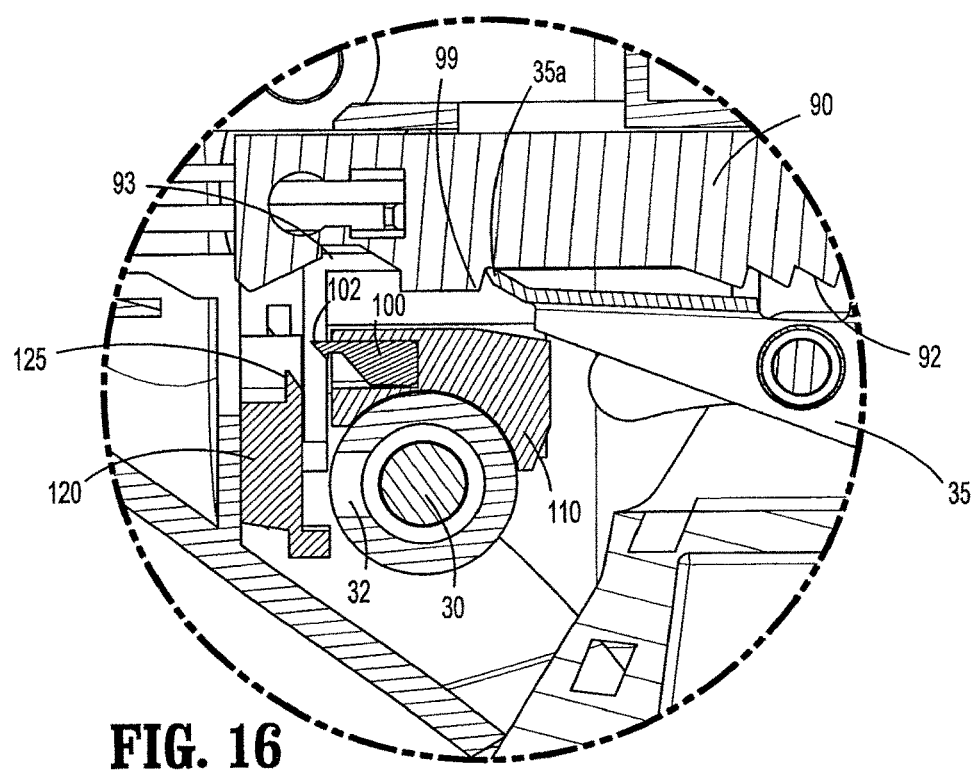
FIG. 16 is a side cross-sectional view taken along section line 16-16 of FIG. 4.

Referring to FIGS. 3 and 5-8, a vertical pawl 120 is slidably positioned in a slot 121 (see FIG. 15) defined between housing half-sections 12a and 12b. Vertical pawl 120 is movable from an extended or upward position in which the tip 125 of vertical pawl 120 engages a cutout 93 formed in the distal end of actuation shaft 90, to a retracted or downward position in which tip 125 of vertical pawl 120 is spaced from actuation shaft 90. A spring 130 supported between housing half-sections 12a and 12b is positioned to bias vertical pawl 120 to the extended position. In the extended position, vertical pawl 120 prevents advancement of actuation shaft 90 to prevent firing of device 10.

A plunger 30 is reciprocably supported between spaced cylindrical channels (not shown) formed in housing half-sections 12a and 12b. Plunger 30 includes a cam member 32. A spring (not shown) may be positioned on each end of plunger 30 within spaced cylindrical channels (not shown) to urge plunger 30 to a position wherein cam member 32 is centrally positioned between a pair of cam surfaces 122 formed on vertical pawl 120 (see FIG. 7). Each cam surface 122 has a recess 124 formed therein for releasably receiving cam member 32 of plunger 30.

Each end 30a of plunger 30 extends through stationary handle 18 and can be pressed against the bias of a spring (not shown) to force cam member 32 into engagement with a respective one of cam surfaces 122 on vertical pawl 120. When cam member 32 is moved into engagement with one of cam surfaces 122, vertical pawl 120 is urged from the extended position to the retracted position to move tip 125 of vertical pawl 120 out of cutout 93 of actuation shaft 90 (see FIGS. 19-23). The positioning of cam member 32 in recess 124 of a respective cam surface 122 retains vertical pawl 120 in the retracted position.

Figure 5:
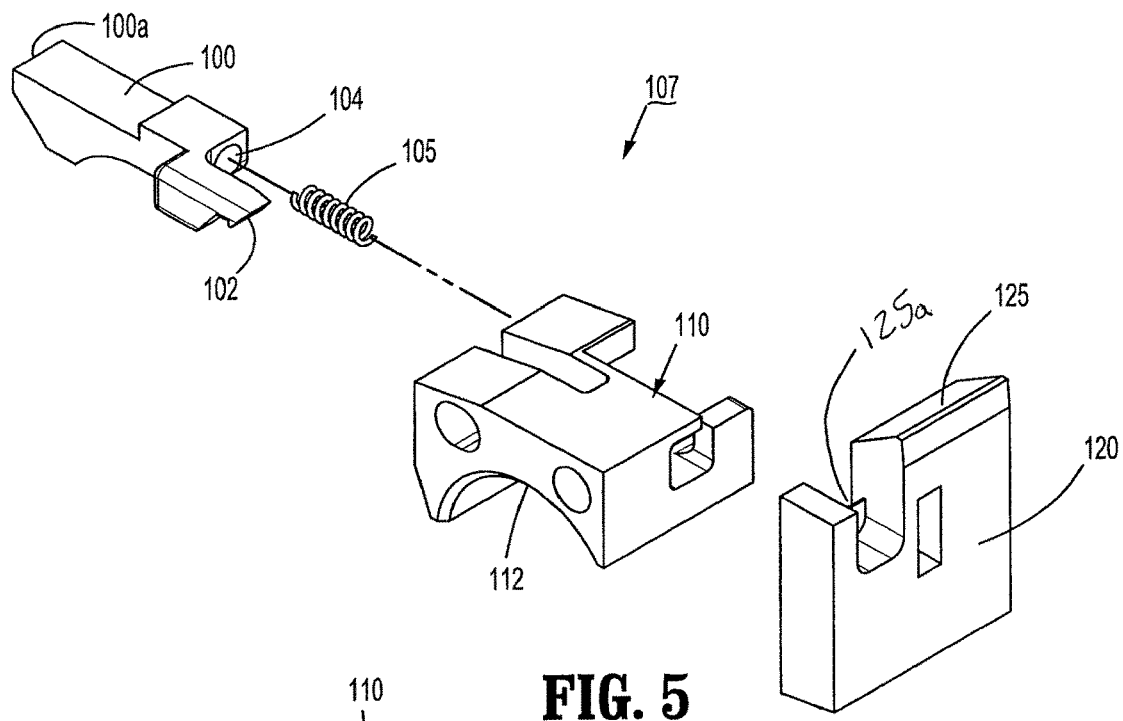
FIG. 5 is an enlarged view of the indicated area of detail shown in FIG. 3.
Figure 6:
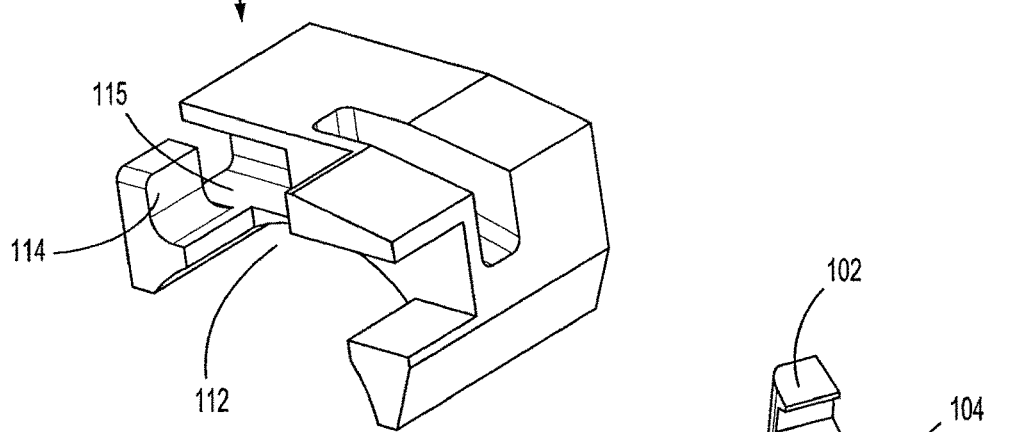
FIG. 6 is a perspective view of the spring support of FIG. 5.
Figure 7:
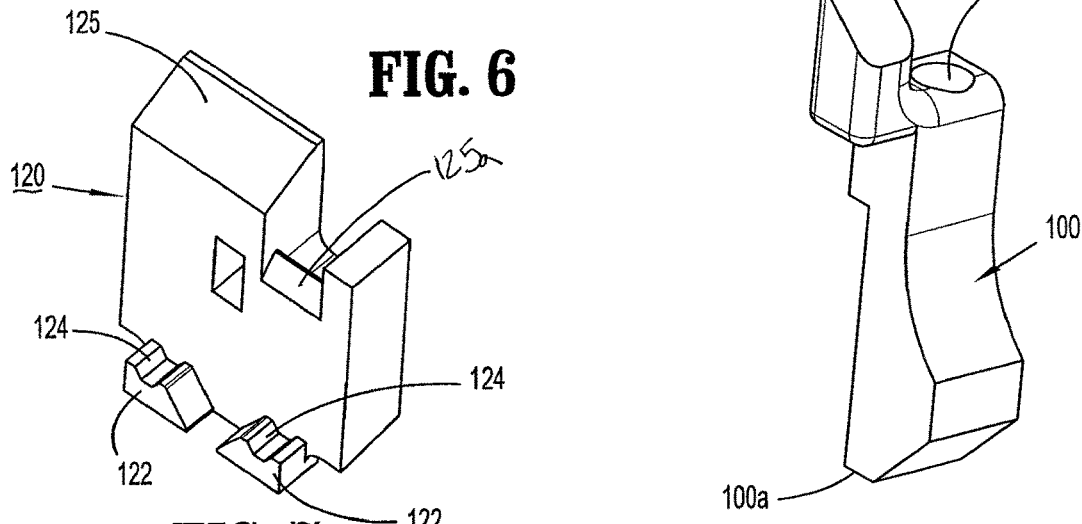
FIG. 7 is a perspective view of the vertical pawl of FIG. 5.
Figure 8:
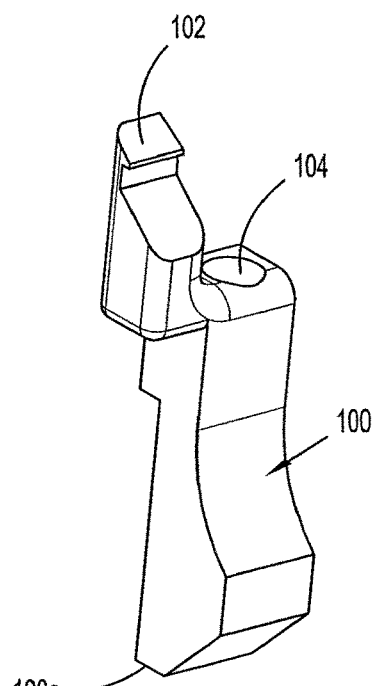
FIG. 8 is a perspective view of the locking cam of FIG. 5.
Figures 12, 13:
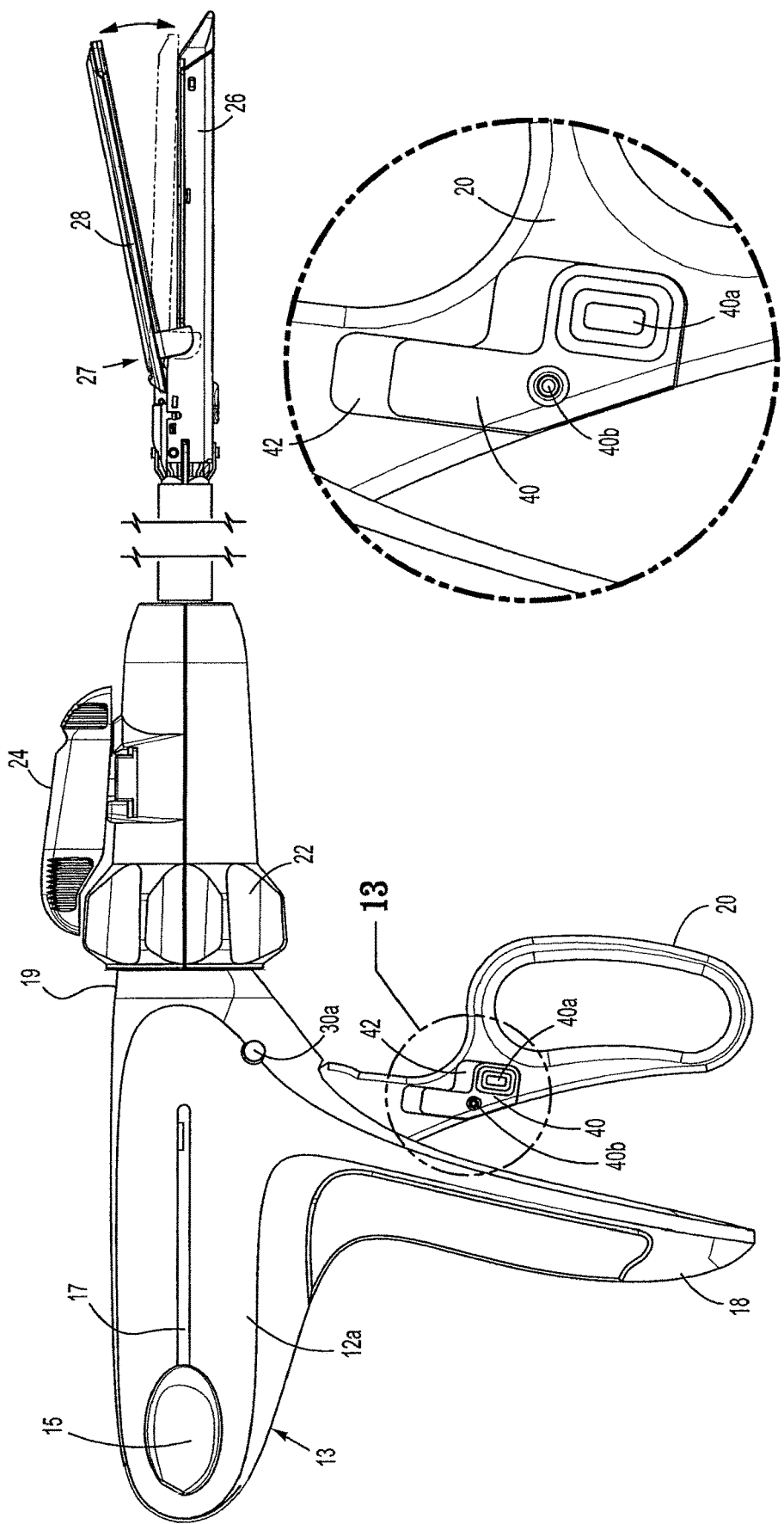
FIG. 12 is a side view of the surgical stapling device shown in FIG. 1.
FIG. 13 is an enlarged view of the indicated area of detail shown in FIG. 12.

Referring to FIGS. 3 and 5, a locking cam assembly 107 is supported between retracted and advanced positions within barrel portion 19 of housing 12 (see FIG. 1) and includes a spring support 110 and a cam member 100 having a tip 102 and a proximal surface 100a. Plunger 30 is received within an annular recess 112, shown in FIGS. 3 and 5, defined in a bottom side of spring support 110 to maintain spring support 110 between housing half-sections 12a and 12b. Cam member 100 is slidably received in a slot 115 defined in spring support 110. Cam member 100 is movable from an extended or distal position in which tip 102 of cam member 100 engages tip 125 of vertical pawl 120, to a retracted or proximal position in which tip 102 of cam member 100 is spaced from vertical pawl 120. In the retracted position, surface 100a of cam member 100 is spaced from spring support 110. Cam member 100 is biased proximally by a spring 105 which is secured at one end to a recess 104 defined in the distal end of cam member 100 and is configured at the opposite end to engage an extension 114 formed by slot 115 in spring support 110. In the extended or distal position, tip 102 of cam member 100 engages tip 125a of vertical pawl 120 to retain vertical pawl 120 in the retracted position.

Referring to FIGS. 3, 9, and 11, movable handle 20 includes a grasping pawl assembly 67 operatively associated with slide buttons 40 and 45. Grasping pawl assembly 67 is configured for movement with respect thereto in response to manipulation of slide buttons 40 and 45. Grasping pawl assembly 67 includes a pawl arm 50 having a sloped surface 55 defined on an outturned portion 52 of a top end of pawl arm 50, and a grasping pawl 60 pivotally supported within outturned portion 52 of pawl arm 50. A top end of slide button 45 includes an in-turned portion 46 having an extension 48a that defines a recessed groove 48. Recessed groove 48 is dimensioned and configured to slidably receive an extension 58a defined by a recessed groove 58 in a bottom end of pawl arm 50. Reciprocally, recessed groove 58 in pawl arm 50 is dimensioned and configured for slidably receiving extension 48a of slide button 45. A bottom end of slide button 45 includes an opening 41a configured to receive a connector pin 44 therethrough. A cylindrical receptacle 40b extends outwardly from an inner surface of slide button 40 and is configured and dimensioned to translate within a longitudinal slot 42a formed in recess 42 of movable handle 20. Connector pin 44 is dimensioned to be received within receptacle 40b to secure slide button 45 to slide button 40. A protrusion 47 is disposed on a lateral surface of slide button 45 configured to be received in a snap-fit manner within a pair of detents 108a and 108b defined within movable handle 20 (see FIG. 4), as will be discussed in further detail below.

Outturned portion 52 of pawl arm 50 includes a recessed groove 53 having a pair of throughbores 57 dimensioned to slidably receive a pivot pin 56. A biasing spring 64 is configured at one end for insertably receiving a pivot pin 62 therein and is insertably received within recessed groove 53 at the other end. Grasping pawl 60 includes a pair of lateral extensions 60b and 60c defining a recess 60a. Pivot pin 56 is received by an opening 61 in a bottom end of grasping pawl 60. Pivot pin 62 is pivotally received within recess 60a, such that grasping pawl 60 is pivotal in a proximal direction about pivot pin 62 in relation to pawl arm 50. Recessed groove 53 is dimensioned to accommodate the pivoted motion of grasping pawl 60 between a straight position, i.e., along the longitudinal axis of pawl arm 50, and a proximal or rearward position. Lateral extension 60b is configured to contact a surface 53a of recessed groove 53, such that the pivoting motion of grasping pawl 60 is restricted to a proximal direction from a straight position with respect to pawl arm 50. Lateral extension 60c is configured to pivot through groove 53 in outturned portion 52 to allow pivoting motion of grasping pawl 60 into the proximal or rearward position. In the proximal or rearward position, lateral extension 60c depresses pivot pin 62, and thus spring 64, within a bore 63 defined in outturned portion 52 (see FIG. 23).

Figure 4:
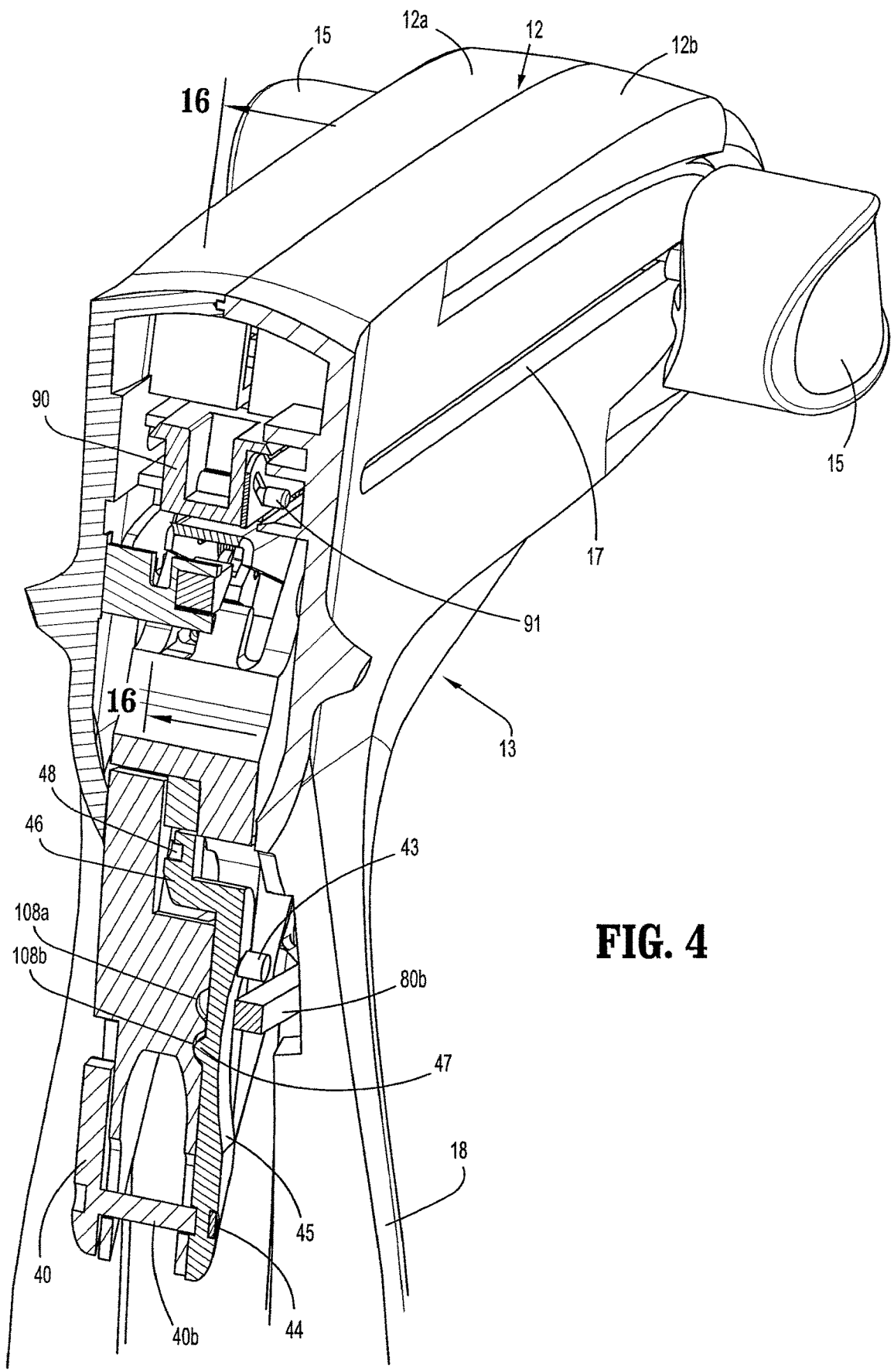
FIG. 4 is a cross-sectional rear perspective view taken along section line 4-4 of FIG. 1.
Figure 17:
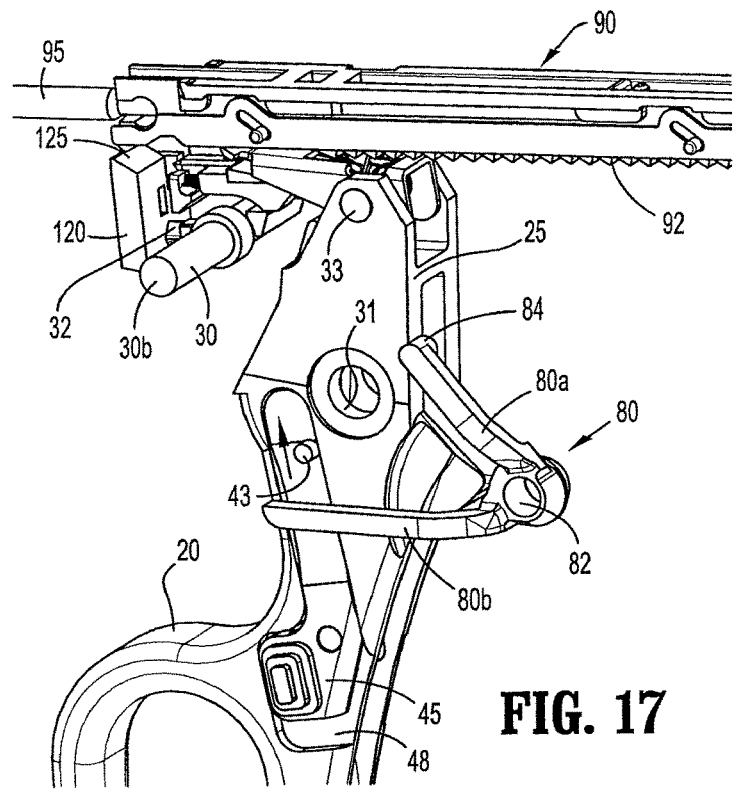
FIG. 17 is a side perspective view with portions broken away of the handle assembly of the surgical stapling device shown in FIG. 1, with the housing removed.
Figure 18:
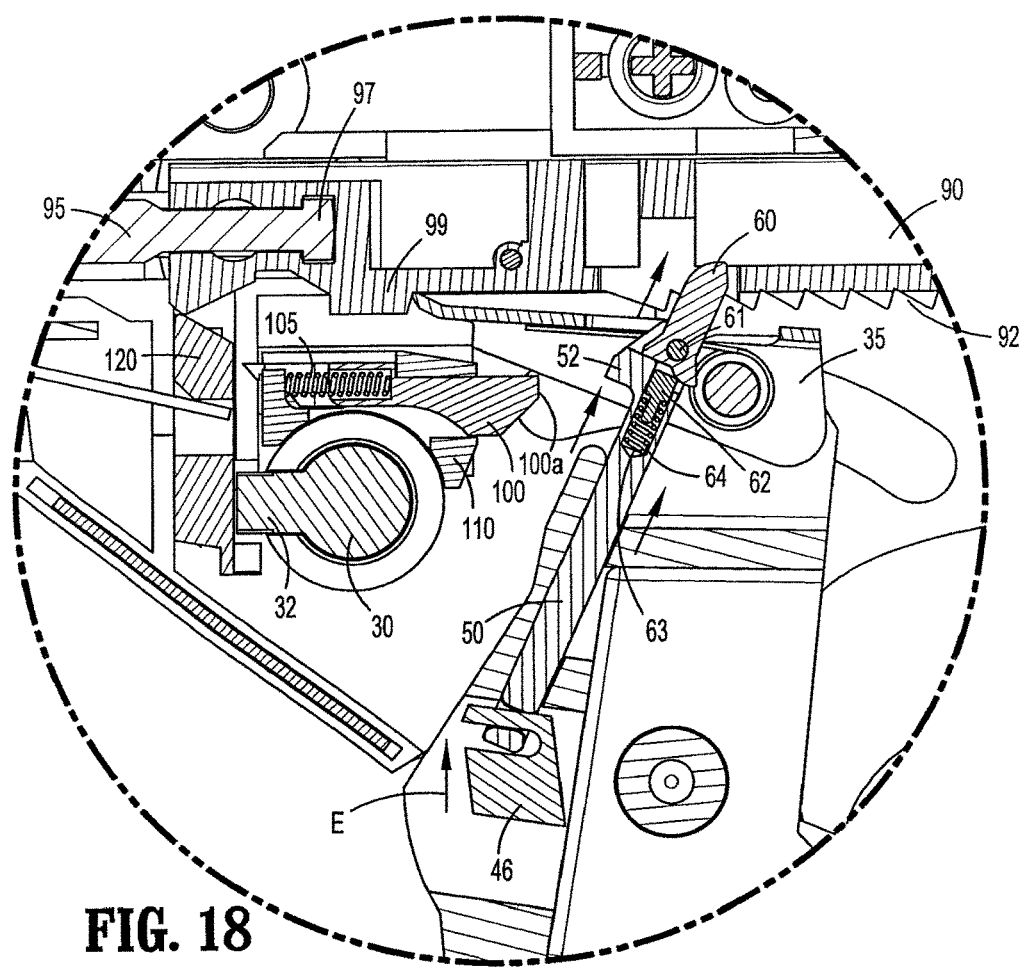
FIG. 18 illustrates the grasping pawl of FIG. 15 engaging the toothed rack.
Figure 23:
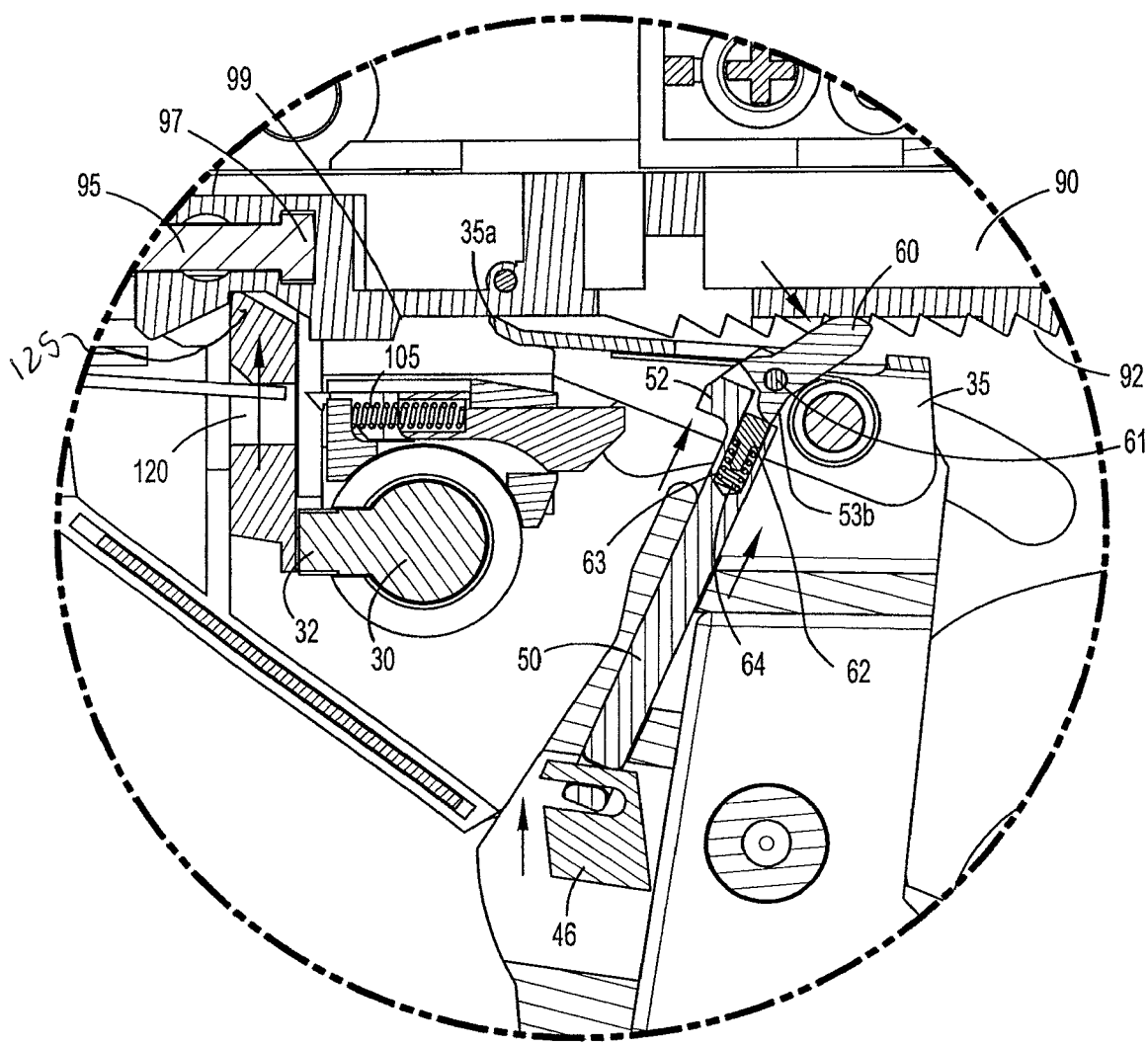
FIG. 23 is a side cross-sectional view, illustrating the vertical pawl in the upward position and slide button in the upward position causing the grasping pawl to engage the toothed rack.

Referring to FIG. 17, handle assembly 13 (see FIG. 1) further includes a yoke 80 configured to return device 10 to the default grasping mode, such that slide buttons 40 and 45 are returned to the upward position to urge grasping pawl 60 into engagement with a slot in the distal end portion of toothed rack 92, as will be discussed in detail below. Yoke 80 is rotatably supported within stationary handle 18 about a cylindrical member (not shown) which is received within an opening 82 within yoke 80. A pair of arms 80a and 80b extend laterally from opening 82. Upon movement of movable handle 20 in the direction indicated by arrow "A" (see FIG. 19), i.e., pivoted towards stationary handle 18, slide buttons 40 and 45 are movable from an upward position in which grasping pawl 60 is engaged in a slot 92b in toothed rack 92 of actuation shaft 90, to a downward position in which grasping pawl 60 is spaced from toothed rack 92 of actuation shaft 90. When grasping pawl 60 is positioned within slot 92b, only limited advancement and retraction of the actuation shaft 90 will occur upon operation of movable handle 20, allowing device 10 to operate in the grasping mode. In the upward position, protrusion 47 on slide button 45 is positioned within detent 108a. Downward movement of slide button 45 causes downward movement of protrusion 47 from detent 108a into detent 108b, as seen in FIG. 4. Reception of protrusion 47 within detents 108a and 108b provides the surgeon with an audible and/or tactile response to indicate a change in position/mode of slide buttons 40 and 45. During movement of movable handle 20 in the direction indicated by arrow "C" (see FIG. 21), i.e., movement towards its initial position that is spaced from stationary handle 18, a cam member 84 formed at the distal end of arm 80a slidably engages a camming surface 25 defined on a proximal side of movable handle 20 effecting clockwise rotation of yoke 80, such that arm 80b of yoke 80 engages a post 43 formed on the top end of slide button 45 to urge slide buttons 40 and 45 in the direction indicated by arrow "E" in FIG. 18 into the upward position. As shown in FIG. 23, grasping pawl 60 is moved downward by slot 92a in toothed rack 92 of actuation shaft 90.

A retraction mechanism which includes retractor knobs 15 (see FIG. 1) is connected to the proximal end of actuation shaft 90 by a coupling rod 96. Coupling rod 96 includes left and right engagement portions 96a and 96b which extend through elongated slots 17 formed in housing half-sections 12a and 12b and are configured to receive retractor knobs 15. A central portion of 96c of coupling rod 96 is dimensioned and configured to be slidably received within a pair of opposed slots 98 formed in actuation shaft 90 adjacent the proximal end thereof. A release plate 70 is supported on one side of actuation shaft 90 by a pair of spaced apart pins 91 (see FIG. 3). Pins 91 extend outwardly from a lateral face of actuation shaft 90 to engage a pair of angled cam slots 71 formed through release plate 70. In this way, release plate 70 is operatively associated with actuation shaft 90 and is mounted for movement with respect thereto in response to manipulation of retractor knobs 15.

In use, when retractor knobs 15 are pulled rearwardly or proximally, coupling rod 96 initially moves release plate 70 rearward in relation to actuation shaft 90 as coupling rod 96 slides in slots 98 of actuation shaft 90. As this occurs, release plate 70 is moved downwardly by pins 91 with respect to actuation shaft 90 thereby covering toothed rack 92 to disengage engaging finger 35a of advancement pawl 35 from toothed rack 92. Once coupling rod 96 reaches a position at which it engages the proximal end of slots 98, additional rearward movement of retractor knobs 15 causes retraction of actuation shaft 90 and thus retraction of control rod 95 rearwardly. Actuation shaft 90 is biased proximally by spring 64 which is secured at one end to coupling rod portion 96c via a connector 75 and at the other end to a post 77 on actuation shaft 90.

Figure 19:
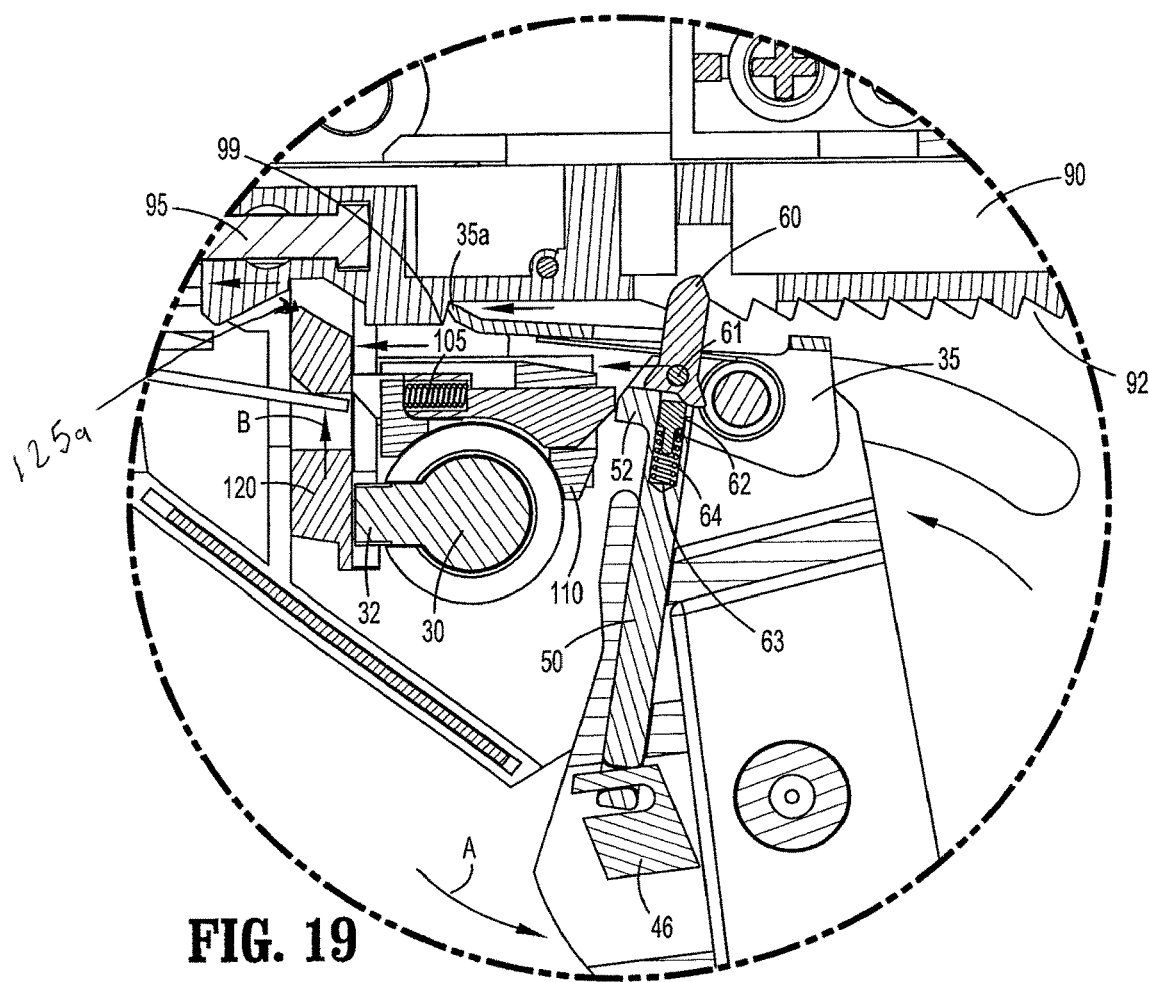
FIG. 19 is a side cross-sectional view, illustrating the movable handle pivoted towards the stationary handle.

Surgical stapling device 10 is initially in the grasping mode. Referring to FIG. 19, movable handle 20 can be manipulated to open and approximate cartridge assembly 26 and anvil assembly 28, back and forth, in a reciprocal fashion. Movable handle 20 is moved in the direction indicated by arrow "A" through a grasping stroke, wherein movable handle 20 is pivoted towards stationary handle 18 against the bias of a torsion spring (not shown) to move engagement finger 35a of advancement pawl 35 into engagement with a shoulder 99 formed on actuation shaft 90. Subsequent movement of movable handle 20 through the grasping stroke rotates pawl arm 50 counter-clockwise. Counter-clockwise rotation of pawl arm 50 causes sloped surface 55 of outturned portion 52 of pawl arm 50 to engage proximal surface 100a of cam member 100, biasing cam member 100 into the extended or distal position. In the extended or distal position, tip 102 of cam member 100 engages tip 125a of vertical pawl 120 to retain vertical pawl 120 in the retracted position (see FIG. 20). In the retracted position, vertical pawl 120 is spaced from actuation shaft 90, allowing actuation shaft 90 to return to the retracted position upon subsequent movement of movable handle 20 in the direction indicated by arrow "C."

Figure 21:
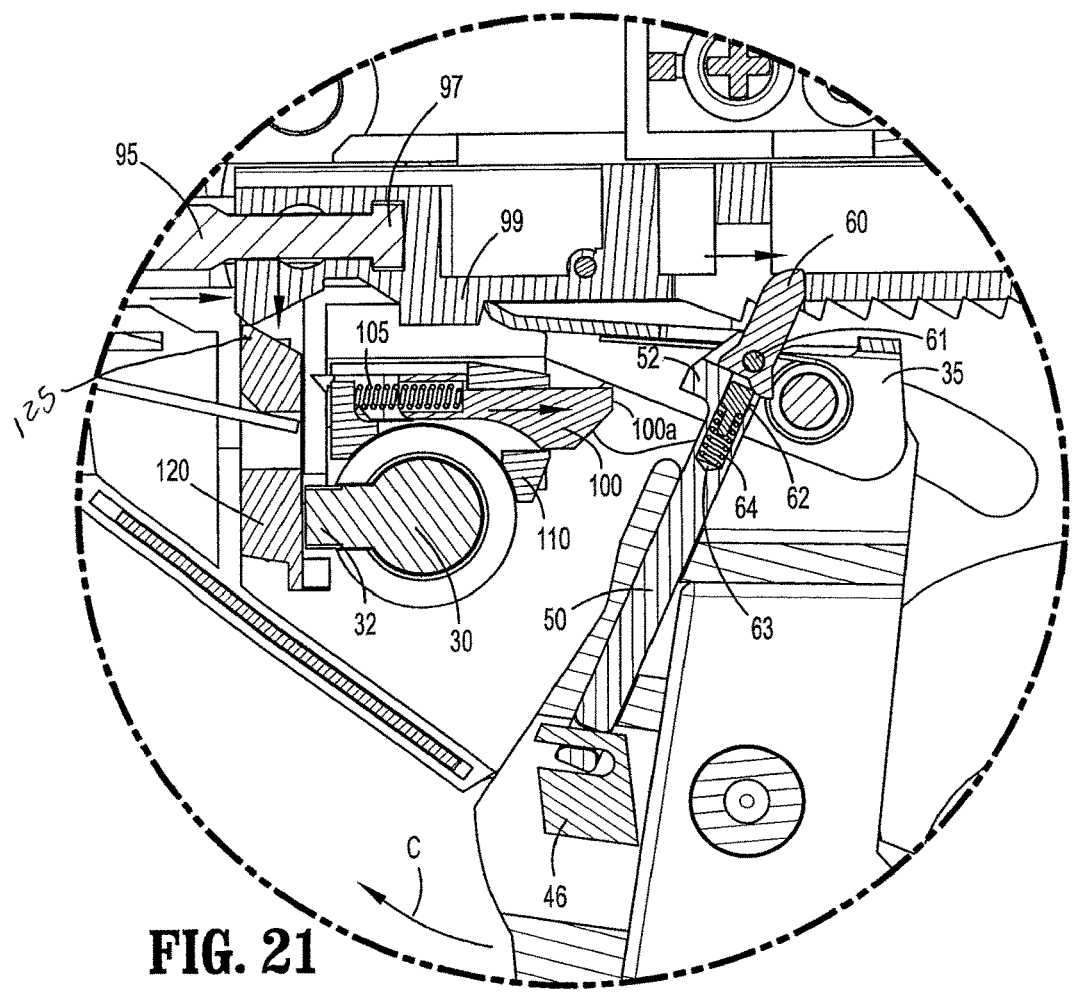
FIG. 21 is a side cross-sectional view, illustrating the movable handle biased away from the stationary handle.
Figure 22:
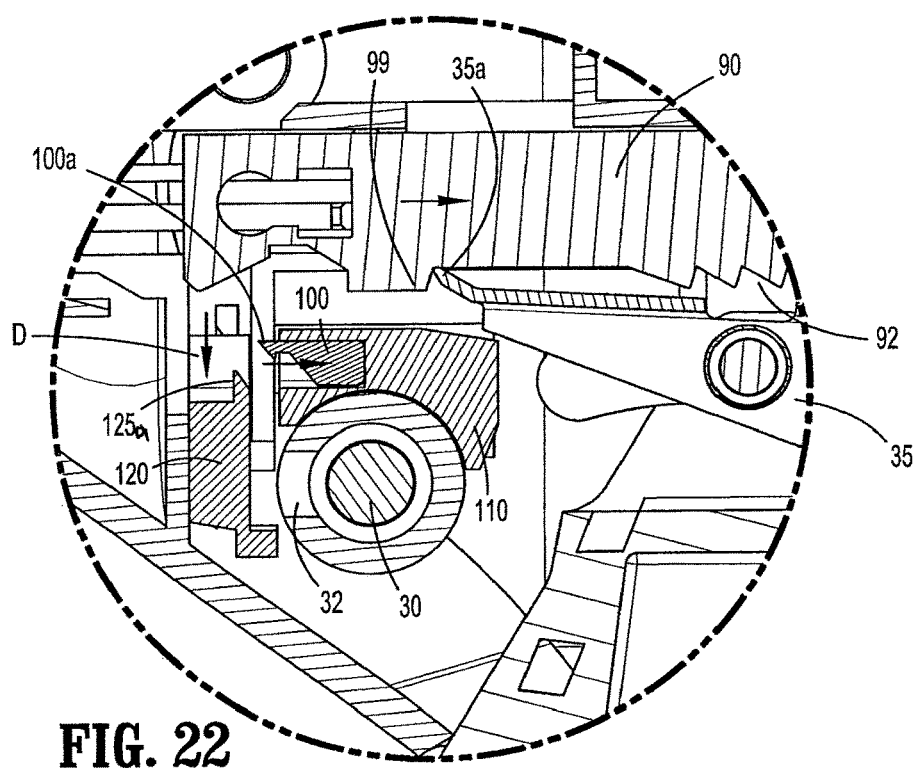
FIG. 22 is a side cross-sectional view, illustrating the actuation shaft in the retracted position.

Referring to FIG. 21, after movable handle 20 is released by the user, a biasing member (not shown) returns movable handle 20 in the direction indicated by arrow "C" to its initial position. As movable handle 20 returns to its initial position, arm 80b of yoke 80 slides slide buttons 40, 45 upwardly, so that device 10 remains in grasping mode. Sliding slide buttons 40, 45 downwardly changes the mode of device 10 to the clamping mode, so that subsequent movement of movable handle 20 in the direction "A" clamps cartridge assembly 26 and anvil assembly 28 onto tissue so that cartridge assembly 26 and anvil assembly 28 will remain approximated even after the movable handle 20 is released. Vertical pawl 120 moves into engagement with cutout 93 in actuation shaft 90 to lock actuation shaft 90 in position. When plunger 30 is pressed inward towards housing half-sections 12a and 12b, cam member 32 of plunger 30 engages cam surfaces 122 of vertical pawl 120 such that cam member 32 is releasably received in recesses 124 to urge vertical pawl 120 in the direction indicated by arrow "D" in FIG. 22 to its retracted position. In the retracted position, tip 125 of vertical pawl 120 is outside of cutout 93 in actuation shaft 90. Vertical pawl 120 is maintained in the retracted position by engagement between cam member 32 of plunger 30 and recesses 124 on cam surfaces 122 of vertical pawl 120.

As movable handle 20 returns to its initial position and urges yoke 80 to rotate clockwise. Clockwise rotation of yoke 80 forces arm 80b of yoke 80 to engage post 43 on slide button 45 to urge slide buttons 40 and 45 into the upward position. In the upward position, grasping pawl 60 is pivotally biased downward by slot 92a in toothed rack 92, instead of slot 92b, as toothed rack 92 has been advanced (see FIG. 23). Device 10 is now in a fire-ready mode. The movable handle 20 can be actuated by moving the movable handle in the direction "A" to advance the actuation shaft 90, deploying staples from the cartridge assembly 26. Movable handle 20 is moved in the direction indicated by arrow "A" in FIG. 19 through a second, firing stroke, during which advancement pawl 35 engages toothed rack 92 of actuation shaft 90 to advance actuation shaft 90 and control rod 95 distally. Referring again to FIG. 19, as actuation shaft 90 moves distally, shoulder 99 formed on actuation shaft 90 engages vertical pawl 120 to move vertical pawl 120 downwardly to disengage cam member 32 of plunger 30 from cam surfaces 122 of vertical pawl 120 and allow spring (not shown) to return plunger 30 to the neutral position, i.e., in a non-compressed position. Subsequent motion of movable handle 20 in the direction indicated by arrow "C" in FIG. 21 further advances toothed rack 92. Retractor knobs 15 are used to retract actuation shaft 90 and thus control rod 95 rearwardly, realigning grasping pawl 60 within slot 92b of toothed rack 92. Device 10 is in the grasping-ready mode, as the yoke 80 maintains slide button 45 in the upward position.

Often in endoscopic procedures, tissue must be manipulated or pulled aside to allow surgeons to access and/or view the tissue site before clamping and stapling can be performed. Selectable modes of operation appreciated by the present disclosure allows surgeons the benefit of operating device 10 in the grasping mode wherein tool assembly 27 may be manipulated by operation of movable handle 20 to grasp and manipulate tissue before easily switching device 10 to the clamping mode of operation wherein tool assembly 27 is configured to clamp tissue and apply staples.

Figure 14:
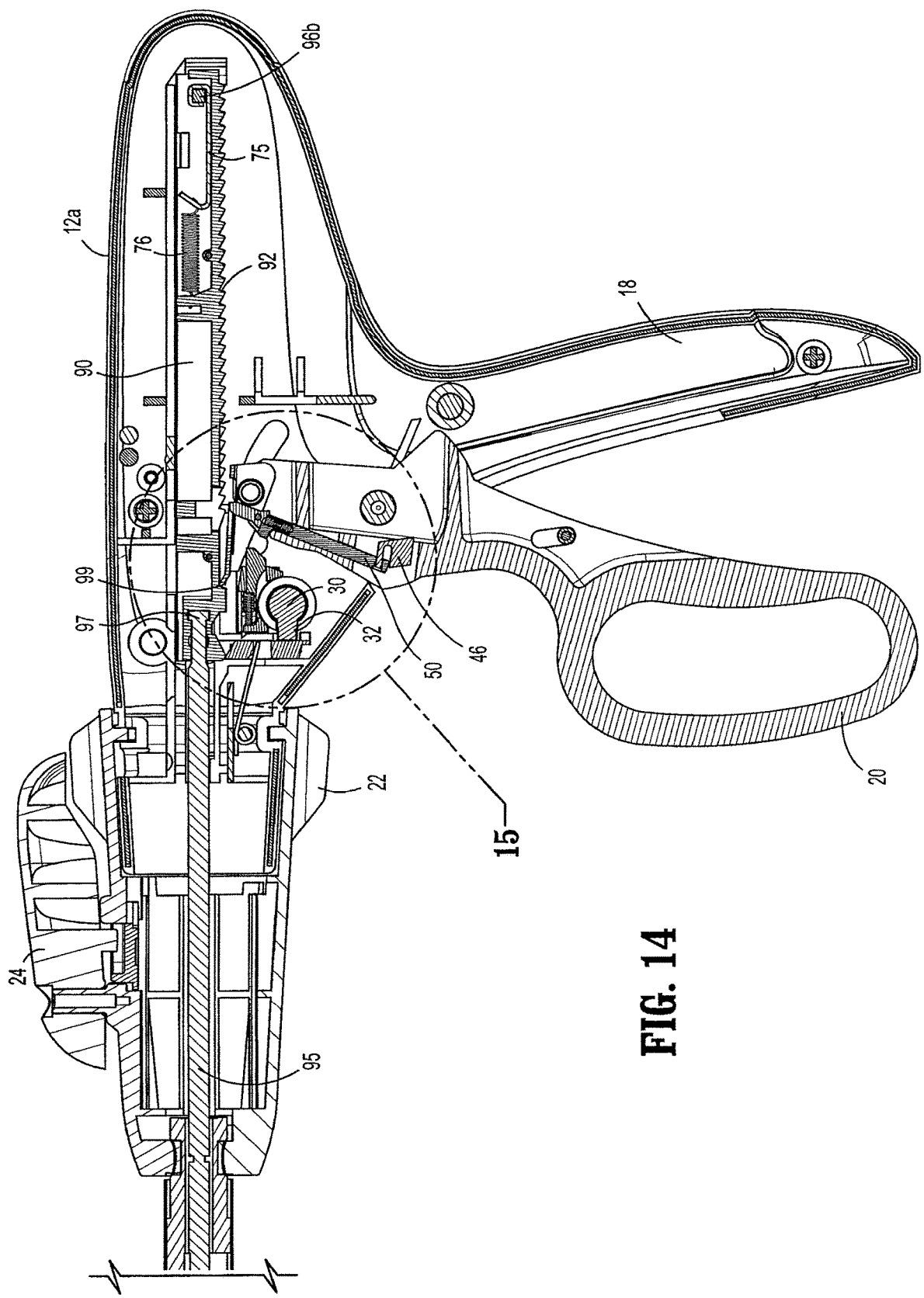
FIG. 14 is a side cross sectional view of the handle assembly of FIG. 1.

FIG. 14 illustrates operation of the retraction mechanism of device 10. In use, when retractor knobs 15 are pulled rearwardly by a surgeon, coupling rod 96 initially moves release plate 70 rearwardly in relation to actuation shaft 90 as coupling rod 96 slides in slots 98 of actuation shaft 90 such that pins 91 cam release plate 70 downwardly to a position covering toothed rack 92 of actuation shaft 90 and disengaging finger 125 of pawl 120 from toothed rack 92. When coupling rod 96 is pulled rearwardly to a position at which it engages the back end of slots 98, additional rearward movement of retractor knobs 15 will effect proximal movement of actuation shaft 90 and control rod 95.

In an alternative embodiment, surgical stapling device 10 may be provided with a grasping mode, but without plunger 30. In this embodiment, vertical pawl 120 and locking cam assembly 107 are removed.

Figure 20:
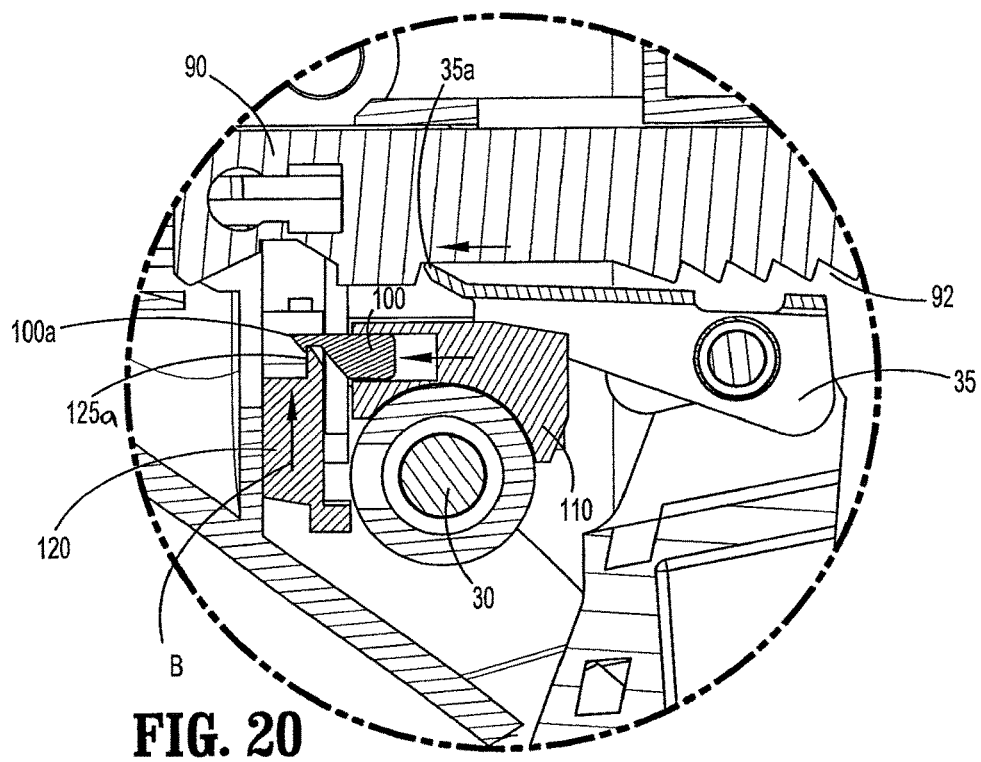
FIG. 20 is a side cross-sectional view, illustrating the vertical pawl biased into the downward position by the locking cam.

Device 10 starts in grasping mode, per FIGS. 19 and 20. Movable handle 20 can be moved back and forth to open and close the jaws of tool assembly 27 as grasping pawl 60 is engaged in slot 92b. Vertical pawl 120 and locking cam assembly 107 are removed in this embodiment.

Sliding slide buttons 40, 45 down moves grasping pawl 60 away from slot 92b. When movable handle 20 is manipulated to clamp tissue, grasping pawl 60 moves into slot 92a. As movable handle 20 is further manipulated, advancement pawl 35 advances toothed rack 92 and fires staples. Multiple strokes of movable handle 20 are used to advance toothed rack 92, with advancement pawl 35 repeatedly engaging and disengaging toothed rack 92. Yoke 80 maintains slide buttons 40, 45 in the upward position during firing. After retractor knobs 15 are used to retract toothed rack 92, grasping pawl 60 is aligned with slot 92b and device 10 is in the grasping mode again.

It will be understood that various modifications may be made to the embodiments disclosed herein. For example, it is envisioned that the surgical stapling device disclosed may be used in association with other surgical devices, e.g., clip appliers, dissectors, electrosurgical sealing devices, etc. Further, the device may also include tool assemblies other than staplers or those devices which eject a fastener, e.g., sealing devices (electrosurgical and non-electrosurgical), etc. The button or other actuator for changing the mode of operation for the device may be provided on one side or both sides of the handle assembly. Therefore, the above description should not be construed as limiting, but merely as exemplifications of preferred embodiments. Those skilled in the art will envision other modifications within the scope and spirit of the claims appended hereto.

What is claimed:

1. A surgical stapling device comprising:
   a handle assembly including a stationary handle portion and a trigger that is movable in relation to the stationary handle portion, the handle assembly including a pivotable pawl and a slidable pawl, the pivotable pawl and the slidable pawl supported on the trigger and movable with the trigger in relation to the stationary handle portion, the handle assembly having a drive member engageable by the pivotable pawl and the slidable pawl; and
   a tool assembly mounted to the handle assembly, wherein the tool assembly is configured to grasp tissue in a first mode of operation and clamp tissue in a second mode of operation, the slidable pawl engaged with the drive member in the first mode of operation and the pivotable pawl engaged with the drive member in the second mode of operation.

2. The surgical stapling device of claim 1, further including an elongated member defining a longitudinal axis, the elongated member having a proximal portion secured to the handle assembly and a distal portion supporting the tool assembly.

3. The surgical stapling device of claim 2, wherein the handle assembly further includes a rotation knob that is rotatably supported on the handle assembly, the rotation knob supporting the elongated member and being rotatable in relation to the handle portion to rotate the elongated member and the tool assembly in relation to the handle portion.

4. The surgical stapling device of claim 2, wherein the tool assembly is pivotably supported on the distal portion of the elongated member by a pivot member, the pivot member facilitating pivotal movement of the tool assembly from a first position aligned with the longitudinal axis to second positions misaligned with the longitudinal axis.

5. The surgical stapling device of claim 4, wherein the handle assembly further includes an articulation lever, the articulation lever coupled to the tool assembly such that actuation of the articulation lever effects movement of the tool assembly between the first position and the second positions.

6. The surgical stapling device of claim 2, wherein the movable handle and pivotable pawl are operably associated with the drive member such that movement of the movable handle effects axial movement of the drive member.

7. The surgical stapling device of claim 6, wherein the trigger is movable between two positions to advance and retract the drive member in the second mode of operation.

8. The surgical stapling device of claim 7, wherein movement of the trigger towards the stationary portion of the handle assembly moves the drive member distally to clamp tissue within the tool assembly and a movement of the trigger away from the stationary handle moves the drive member proximally to unclamp tissue from within the tool assembly.

9. The surgical stapling device of claim 2, wherein the drive member reciprocates along the longitudinal axis in the first mode of operation.

10. The surgical stapling device of claim 1, wherein the tool assembly includes a cartridge assembly and an anvil assembly, at least one of the anvil assembly and the cartridge assembly being movable in relation to the other between spaced and approximated positions.

11. The surgical stapling device of claim 1, wherein the drive member has teeth and the pivotable pawl engages and disengages the teeth in an alternating fashion as the trigger is moved between the two positions.

12. The surgical stapling device of claim 11, wherein the drive member defines a first slot and a second slot, the slidable pawl positioned within the first slot in the first mode of operation positioned within the second slot in the second mode of operation.

13. The surgical stapling device of claim 12, wherein the movable handle is rotatably supported by the housing.

14. The surgical stapling device of claim 1, further comprising a slidable button mounted on the trigger, the slidable button being movable on the trigger to move the slidable pawl between a first position disengaged from the drive member and a second position engaged with the drive member.

* * * * *